United States Patent [19]
Altshuler

[11] Patent Number: 5,873,875
[45] Date of Patent: Feb. 23, 1999

[54] DEVICE FOR USE IN THE LASER TREATMENT OF BIOLOGICAL TISSUE

[76] Inventor: Grigory Borisovitch Altshuler, Poulkovskoje shosse d.5, kl kv197, 196240 St. Petersburg, Russian Federation

[21] Appl. No.: 894,396
[22] PCT Filed: Sep. 27, 1995
[86] PCT No.: PCT/RU95/00211
    § 371 Date: Aug. 18, 1997
    § 102(e) Date: Aug. 18, 1997
[87] PCT Pub. No.: WO96/25979
    PCT Pub. Date: Aug. 29, 1996

[30] Foreign Application Priority Data

Feb. 24, 1995 [RU] Russian Federation ............. 95102749

[51] Int. Cl.⁶ .................................................. A61B 17/36
[52] U.S. Cl. .................... 606/10; 606/16; 606/18
[58] Field of Search ........................... 606/10–13, 16–18; 607/88, 89, 93

[56] References Cited

U.S. PATENT DOCUMENTS

| | | | |
|---|---|---|---|
| 4,408,602 | 10/1983 | Nakajima | 606/10 |
| 4,836,203 | 6/1989 | Miiller et al. | |
| 5,003,977 | 4/1991 | Suzuki et al. | 606/10 |
| 5,071,417 | 12/1991 | Sinofsky | 606/10 |
| 5,098,427 | 3/1992 | Hessel et al. | 606/11 |
| 5,139,494 | 8/1992 | Freiberg | 606/10 |
| 5,325,393 | 6/1994 | Nighan, Jr. et al. | 606/18 |
| 5,387,211 | 2/1995 | Saadatmanesh et al. | 606/10 |
| 5,505,724 | 4/1996 | Steinert | 606/12 |
| 5,746,735 | 5/1998 | Furumoto et al. | 606/10 |

FOREIGN PATENT DOCUMENTS

| | | |
|---|---|---|
| 0 320 080 A1 | 6/1989 | European Pat. Off. |
| 0 429 297 A3 | 5/1991 | European Pat. Off. |
| 0 253 734 A1 | 1/1988 | France |
| WO 90 12548 | 11/1990 | WIPO |

*Primary Examiner*—Max Hindenburg
*Assistant Examiner*—Bryan K. Yarnell
*Attorney, Agent, or Firm*—Marshall, O'Toole, Gerstein, Murray & Borun

[57] ABSTRACT

Two or three pulsed laser (3, 4, 20) devices are provided with a system for the automated optimization of the parameters of radiation produced by these lasers as well the types and regimes of processing of each kind of tissue. The outputs of at least one detector (15) of information about the status of tissue (16) that is under processing are connected to the inputs of control unit 1 which output signals are applied to electronic switchers (5, 6, 26) placed in the circuits connecting the power supply (2) with each of lasers (3, 4, 20). The devices also include the controlled system of treatment zone irrigation (17) and a system for laser radiations mixing consisting of reflective (7, 21) and selective (8, 25) mirrors that makes it possible to provide the independent radiation outputs.

12 Claims, 2 Drawing Sheets

DEVICE FOR USE IN THE LASER TREATMENT OF BIOLOGICAL TISSUE

BACKGROUND OF THE INVENTION

The invention concerns to medical engineering and can be used in surgery, orthopedy and dentistry for processing of soft and hard tissues.

It is known the device for dental tissue laser processing, (patent WO 90/01907, A61C 5/00, date of the publication 08.03.90), comprising the consequently placed along an optical axis the pulsed laser and means of delivery of radiation to a tooth, including a piece of an optical fiber which input is optically conjugated with laser output, and tip which input is optically conjugated with optical fiber's output and its output is the output of device. In this device neodymium, holmium and erbium lasers may be used.

The main disadvantage of above device is that it is impossible to make quick replacement of one laser on other depending on a kind of a tissue under processing, and also high danger of a laser trauma.

It is known also the laser device for the treatment of teeth which is the closest one from the technical point of view and can be accepted as a prototype (patent WO 90/12548, And 61-5/00, date of the publication 01.11.90)

This device comprises the control unit, two pulsed lasers, which optical axes are parallel, focusing system and piece of an optical fiber with a tip placed on an optical axis of the second laser. On the optical axes of both lasers there are mirrors which are optically conjugated with each other, focusing system and optical fiber and placed under 45° angle to laser optical axes. The mirror placed on the axis of the first laser is reflective one, and the mirror placed on the axis of the second laser is dichroic one i.e. it selectively reflects the radiation on first laser wavelength and is transparent on the wavelength of the second laser radiation.

The main disadvantage of this device is the insufficient efficiency of its application while the transition from one type of processing to other and the danger of a laser trauma because of absence of a system providing the detection of tissue that is under processing.

SUMMARY OF THE INVENTION

The problem solved by present invention consists of the creation of the device for laser processing of a tissue performing all kinds of laser operations in surgery, orthopedy and dentistry and keeping the opportunities of quick transition from one type of processing to other and minimum invasion.

The specified problem is solved under the realization of the invention due to achievement of technical result consisting of optimization of processing regimes and parameters of laser radiation depending on a type of processing and a kind of a tissue.

The specified technical result under realization of the invention is achieved due to the device for laser processing of a tissue comprising the control unit which outputs are connected with the laser power supply, pulsed lasers which optical axes are parallel, optically conjugated reflective mirror and mirror that is selectively reflective on the wavelength of the first laser and transparent on the wavelength of the second laser both placed on the axes of the first and the second laser respectively, focusing system and optical fibre with a tip placed on the optical axis of the second laser thus the tip's output is the output of the device additionally comprises at least one detector of the information about status of a tissue that is under laser processing which input is conjugated with the place of laser-tissue interaction and the output is connected to the input of the control unit which outputs are connected to the inputs of electronic switchers placed in the circuits connecting each laser with the power supply. The reflective mirror is removable and focusing system as well the optical fibre with a tip are placed on the optical axis of the first laser so the said tip's output is another optical output of the device.

The specified technical result with more efficiency is achieved due to the device for laser processing of a tissue comprising the control unit which outputs are connected with the laser power supply, pulsed lasers which optical axes are parallel, optically conjugated reflective mirror and mirror that is selectively reflective on the wavelength of the first laser and transparent on the wavelength of the second laser both placed on the axes of the first and the second laser respectively, focusing system and optical fibre with a tip placed on the optical axis of the second laser thus the tip's output is the output of the device additionally comprises third pulsed laser which optical axis is parallel to the optical axes of two said lasers, reflective mirror placed on the optical axis of third laser. All the reflective mirrors are removable. Second dichroic mirror is placed on the optical axis of the second laser consequently to the first dichroic mirror. The second dichroic mirror reflects the radiation on the wavelength of the third laser, transmits the radiation on the wavelengths of the first and the second lasers and is optically conjugated with the reflective mirror placed on the optical axis of the third laser, focusing system and input of optical fiber placed on the optical axis of the second laser. Besides on optical axes of both the first and third lasers the focusing system and optical fibre with a tip are placed consequently. The outputs of said tips are the optical outputs of the device. The device is also supplied with at least one detector of the information about the status of a tissue that is under laser processing which input is conjugated with the place of laser-tissue interaction and the output is connected to the input of the control unit which outputs are connected to the inputs of electronic switchers placed in the circuits connecting each laser with the power supply.

The detector of the information about the status of a tissue can be represented by spectral analyser in the range 200–1500 nm which input is optically conjugated with the place of laser-tissue interaction and consists of dispersive element, photodiode array and comparator. The detector of the information about the status of a tissue can also be represented by the infra-red photo-electric detector which input is optically conjugated with the place of laser-tissue interaction by means of folded mirror placed on the optical axis of a laser between output laser mirror and the focusing system through the spectral filter that prevents the detector against the laser radiation.

The detector of the information about the status of a tissue can be represented also by the acoustic detector placed so that the direction of its maximum sensitivity makes with the direction of an optical axis of a tip an angle $\alpha$ that satisfies a condition: $11°<\alpha<86°$. The electronic switcher can be represented by semiconducting or electrovacuum device.

Additionally the device is supplied with a system of processing zone irrigation consisting of the tank for water with the water pump and the air compressor which appropriate outputs are jointed inside the tips and represent the irrigation outputs of the device. The air compressor in a place of connection with air-tubes is supplied with electromagnetic valves connected to the outputs of the control unit through the lines of delay.

It is known that the efficiency of laser processing of a tissue providing the low invasion (necrosis degree) depends on the wavelength and power of laser radiation, energy and duration of laser influence and (for some kinds of tissues) the presence of liquid irrigation of irradiated zone (see, for example, Proceeding of . . . Laser-Tissue Interaction V 24–27, January 1994, Los Angeles, Calif. v.2134A).

The investigations carried out by the author show that it is necessary to make simultaneous optimization of said parameters for each kind of tissue. So it is necessary to provide:
1. The choice of optimum laser wavelengths or their mixture,
2. The detection of laser destruction process, kind and status of tissue. The control of wavelength, power, energy of laser radiation and duration of laser influence.
3. The irrigation of irradiated zone of a tissue.

The set of entered in the device at least one detector of the information about the status of a tissue that is under laser processing which output is connected to the input of the control unit and electronic switchers placed in the circuits connecting the lasers with the power supply and controlled by the output signals from the control unit represents the feedback system which provides the automatic check and optimum control of laser radiation parameters in dependence on kind and status of tissue. So the minimum invasion of laser processing may be achieved.

The necessity of the automatic check and control is caused by frequently arising impossibility of visual determination of kind and status of a tissue that is under laser processing.

The presence of two independent outputs in one device due to an opportunity to remove a reflective mirror from the optical path of the radiation produced by the first laser and the opportunity of mixing of radiations of two lasers increase the efficiency of laser processing of a tissue.

The presence of three lasers with various radiation wavelengths and independent outputs in one device for processing of a tissue and the opportunity of radiation mixing provide the greatest mobility of application of the device and as much as possible expands the field of its application. For example, under the simultaneous influence of holmium and neodymium laser radiations on plentiful blood organs the danger of blood flow caused by the unauthorized punching of large blood vessels is excluded and the combination of radiations of erbium, neodymium and holmium lasers is effective under the processing of bone tissues and hard dental tissues. To provide the mixing of radiation of the third laser with two other ones or each of them the reflective and selective mirrors placed on the axes of third and second lasers respectively are introduced. The opportunity to remove the reflective mirrors from the optical path of the radiation and the presence of additional focusing systems and optical fibers provide the independence of three optical outputs of the device.

The irrigation system introduced additionally in the device being controlled by electromagnetic valves connected to the outputs of the control unit provides the optimum combination of irradiation and irrigation regimes.

The author suppose that the set of claims is the new one as well the engineering satisfies the criterion of invention.

BRIEF DESCRIPTION OF THE DRAWINGS

The subject of the invention is specified by the figures, where.

DETAILED DESCRIPTION OF THE PREFERRED EMBODIMENTS

Figure 1:
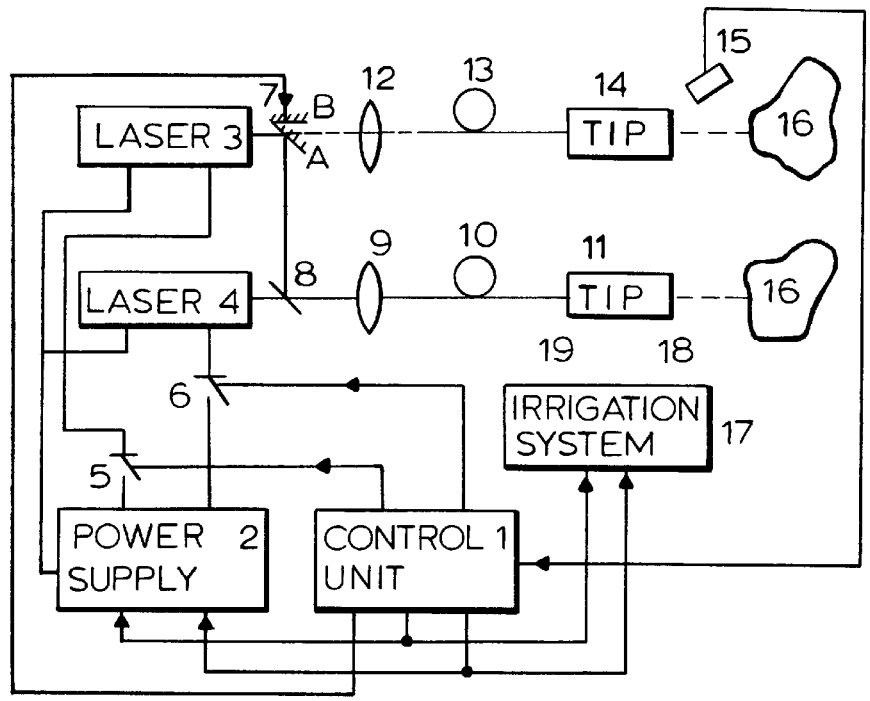
FIG. 1 represents the scheme of the device for laser processing of a tissue.

The device for laser processing of a tissue (FIG. 1) consists of the control unit 1, power supply 2 connected to control unit, pulsed lasers 3,4, connected with the power supply through the electronic switchers 5,6 which are connected to the outputs of the control unit 1. On the optical axes of lasers 34 the reflective mirror 7 and selective mirror 8 are placed, respectively. These mirrors are optically conjugated with each other, focusing system 9 and the output edge of an optical fiber 10 with a tip 11 placed on the optical axis of the laser 4. The selective mirror 8 reflects the radiation of the laser 3 but transmits the radiation of the laser 4. The reflective mirrors 7 placed on the optical axis of the laser 3 is connected to the output of the control unit 1. According to position A it is placed under 45° angle to an axis, and in position B it is parallel to it. The focusing system 12, optical fiber 13 with a tip 14 are placed consequently after the mirror on this axis. The electrical output of the detector of the information about the status of a tissue 15 is connected to the input of the control unit 1. The input of the detector is conjugated with the place of laser-tissue interaction 16. The irrigation system 17 is connected to the same outputs of the control unit 1, as power supply 2 and its water and air outputs 18 and 19 are joined inside the tip 11 (14).

Figure 2:
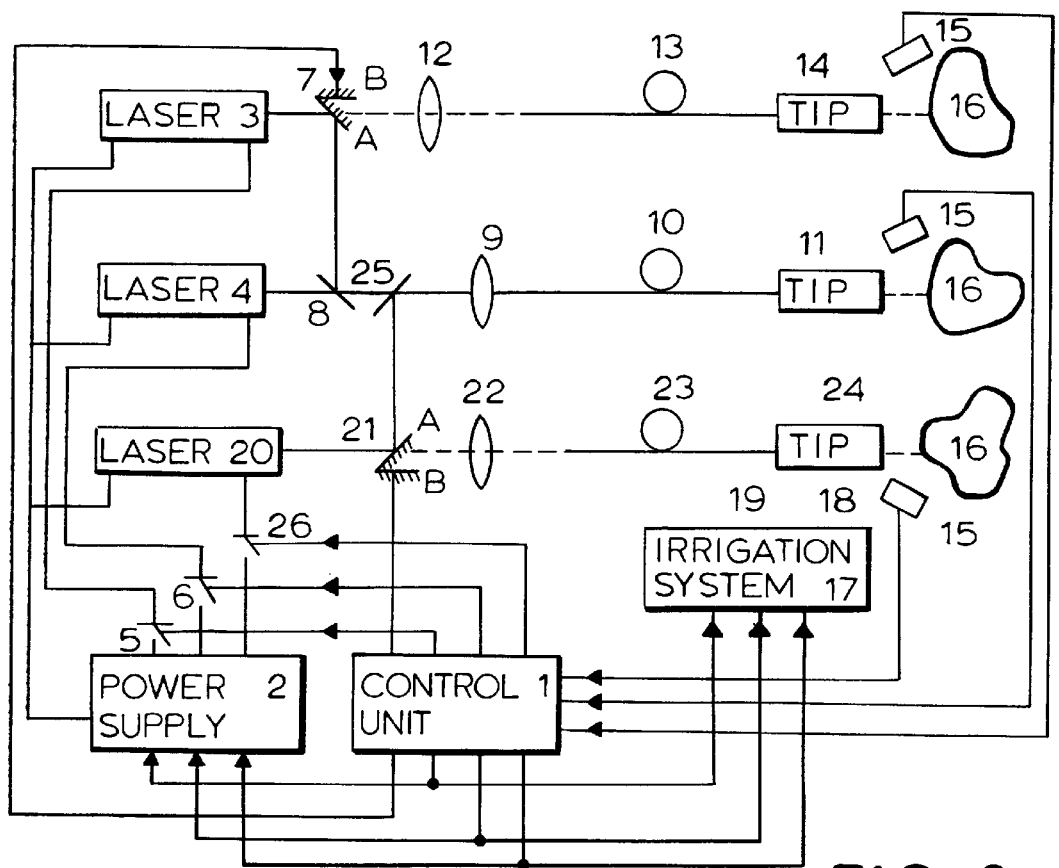
FIG. 2 shows the scheme of the device while three lasers are applied.

The version of the device with three lasers 3,4,20 is represented in FIG. 2. The reflective mirror 21 is placed on the optical axis of laser 20. This mirror as the reflective mirror 7 is connected to the output of the control unit 1. According to position A it is placed under 135° angle to an axis, and in position B it is parallel to it. On the same optical axis the focusing system 22 and the output edge of an optical fiber 23 with a tip 24 are placed. The second selective mirror 25 optically conjugated with the mirror 21, focusing system 9 and the output edge of an optical fiber 10 is placed between focusing system 9 and selective mirror 8. The selective mirror 25 reflects the radiation of the laser 20 but transmits the radiations of the lasers 3,4. The power supply 2 is connected to the laser 20 through the electronic switcher 26.

Figure 3:
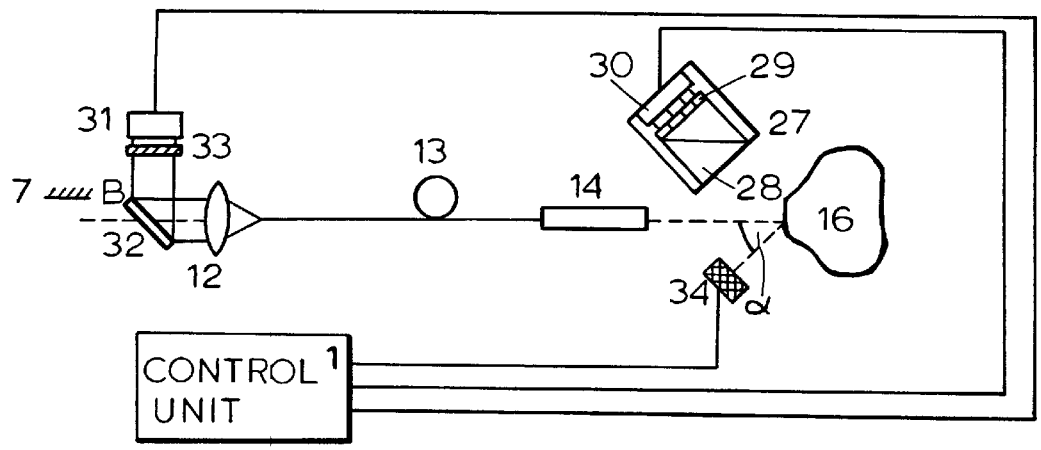
FIG. 3 represents the schemes of arrangement of detectors of the information about the status of a tissue that is under laser processing.

The different versions of the detector 15 of the information about the status of a tissue 16 can be as the spectral analyser 27 (FIG. 3) which input is optically conjugated with the place of laser interaction with tissue 16 consisting of dispersive element 28, photodiode array 29 placed in the field corresponding to 200–1500 nm spectral range and comparator 30 so the infra-red photo-electric detector 31 which input is optically conjugated with the place of laser interaction with tissue 16 by means of optical fiber 13 (10, 23), focusing system 12 (9, 22) and folded mirror 32 placed between focusing system 12 (9, 22) and mirror 8 or directly before the output mirror of the laser 3 (20). Before the optical input of the photoelectric detector 31 the infra-red filter 33 is placed. This spectral filter prevents the detector 31 against the laser radiation. The detector 15 of the information about the status of a tissue 16 can be represented also by the acoustic detector 34 placed near the laser-tissue interaction field so that the direction of its maximum sensitivity makes with the direction of an optical axis of a tip 11 (14,24) an angle $\alpha$ that satisfies a condition: $11°<\alpha<86°$.

Taking into account that the number of detectors of the information about the status of a tissue can change from one up to nine (on each type, about each tip) the number of inputs of the control unit can be equal to nine.

Figure 4:
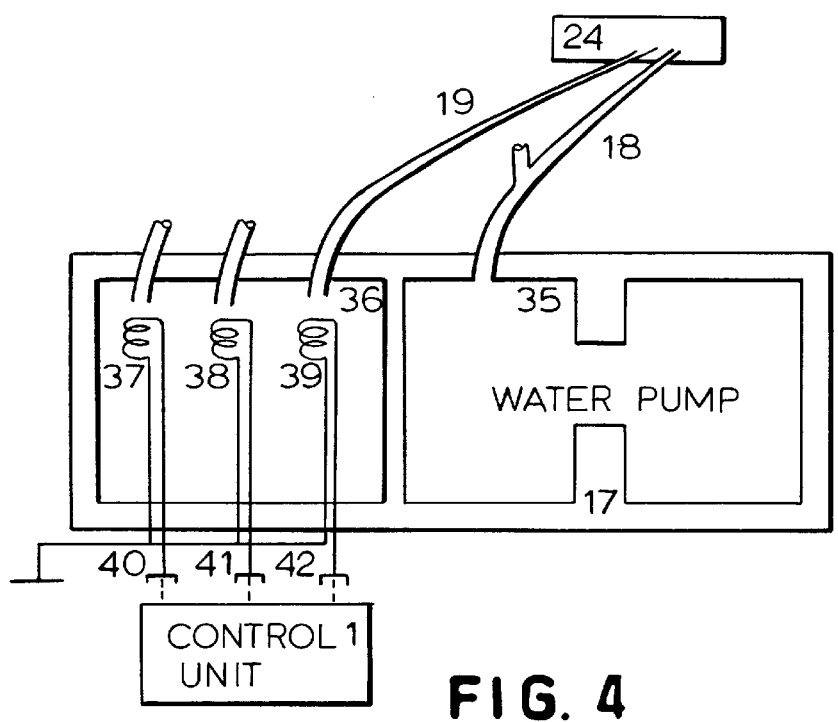
FIG. 4 illustrates the irrigation system.

The system of processing zone irrigation 17 represented in FIG. 4 consists of the tank for water with the water pump 35 connected with air-tube 18 and the air compressor 36. The air-tubes 19 connected to the air compressor 36 are supplied with the electromagnetic valves 37, 38, 39, which are connected through the lines of delay 40, 41, 42 to the same outputs of the control unit 1 as power supply 2.

The device operates as follows. The radiations of lasers 3, 4, 20 while the reflective mirrors 7 and 26 are in B position pass through the focusing systems 9, 12, 22, pieces of optical fibers 10, 13, 23 and the tips 11, 14, 24 and reach the optical outputs of the device.

If the reflective mirrors 7 and 26 are in A position the radiation of the laser 3 is reflected by mirrors 7,8 and then propagates along the optical axis of the laser 4. Similarly, if the laser 20 is presented, the radiation of this laser is reflected by mirrors 21,25 and then propagates along the optical axis of the laser 4. In result, according to the properties of selective mirrors 8 and 25 the radiations of all three lasers can reach the focusing system 9 and the optical output of the tip 11 simultaneously.

The choice of a type of the detector 15 of the information about the status of a tissue 16 depends on a kind of a tissue, processing mode, and also on a kind of a tip. While the non-contact tips are used the main part of emission plume radiation arising under laser processing of a tissue is within the visible and near IR and UV spectral ranges (200–1500 nm). So it is impossible to make the visual observation of kind and status of a tissue.

The spectrum of emission plume radiation depends on kind of a tissue so it is necessary to perform the spectral analysis of this radiation which reaches the dispersive element 28, spectral analyser 27 and photodiode array 29 connected to the comparator 30. The level of output comparator 30 signal corresponds to the definite combination of wavelengths of emission plume radiation. The electrical signal from the comparator 30 of spectral analyser 27 reaches the input of control unit 1 which then produces the signal of change of laser operation mode.

The work with contact tips is connected with the heating of the output edge of a working tool (fiber or sapphire tip) by laser radiation up to certain temperature sufficient for destruction of a tissue. The heating of a place of laser influence stimulates the appearance of infra-red radiation which propagates along a fiber of a tip 11 (14, 24) and a piece of an optical fiber 10 (13, 23) in the direction opposite to the direction of laser radiation propagation. Then it is reflected from the folded mirror 32, and reaches the photo-electric-detector 31 through the infra-red filter 33. The electrical signal from the output of the photo-electric detector 31 reaches the control unit 1 where depending on parameters of this signal the signal of termination, continuation or change of laser operation mode is produced.

It is experimentally found out that the thermal radiation arising during the work with contact tips is in deep infra-red range. In this range the sensitivity of photoelectric detectors is extremely low. The wavelengths of laser radiation are also in infra-red range. Therefore the transmittance spectral band of the filter 33 correlates with the spectral sensitivity of the photoelectric detector 31, with the transmittance band of the fiber 13 and prevents the photo-electric detector 31 against the radiations of lasers 3, 4, 20.

The products of laser destruction of a tissue scatter with supersound speed and due to the fast change of pressure caused by the resistance of environment the acoustic wave is generated. The amplitude of the acoustic wave depends on the kind of tissue. The amplitude of the acoustic wave is registered by the acoustic detector 34. The electrical signal from its output reaches the control unit 1 where a signal of a temporary interruption of laser radiation or change of laser operation mode is synthesized in dependence on the kind of a tissue or in the case of exceeding of laser pulse energy over the tissue laser destruction threshold that influences on laser induced necrosis degree.

The termination (if it is necessary) of laser operation according to signals from photo-electric or acoustic detectors is provided due to fast electronic switchers 5, 6, 26. The signal from the control unit 1 reaches the control input of an electronic switcher 5, (6, 26) then the disconnection of each laser power circuit takes place. The termination of radiation pulse is effective if the time of power switching-off is less than the duration of radiation pulse. (The duration of a laser pulse of radiation can be 150–500 $\mu$s). Therefore fast switchers should be selected. Such fast controlled switchers are the semiconducting or electrovacuum devices which operation time does not exceed 100 $\mu$s.

The irrigation of a tissue by the irrigation system 17 occurs as follows. From the tank for water with the water pump 32 water fills water-tubes 18. In case of necessity of irrigation of a tissue the signals from the control unit 1 reach the electromagnetic valve 37 (38, 39) which opens the path of air under the pressure from the air compressor 36 to the air-tube 19. The ends of water- and airtubes 18 and 19 are placed inside a tip 11 (14, 24) so that water reaches the irrigation outputs of the device under air influence like a spray.

The signals from the control unit 1 reach the electromagnetic valves 37 (38, 39) through the lines of delay 40 (41, 42) simultaneously with the start-generation signals for the lasers 3 (4, 20).

The irrigation of a tissue by water should take place during the intervals between laser pulses (to avoid the undesirable scattering of radiation and to increase the efficiency of irrigation). Therefore the duration of delay provided by the lines of delay 40 (41, 42) is equal to the duration of laser radiation pulses taking into account the time that is need to air to reach the ends of air-tubes 19.

Figure 5:
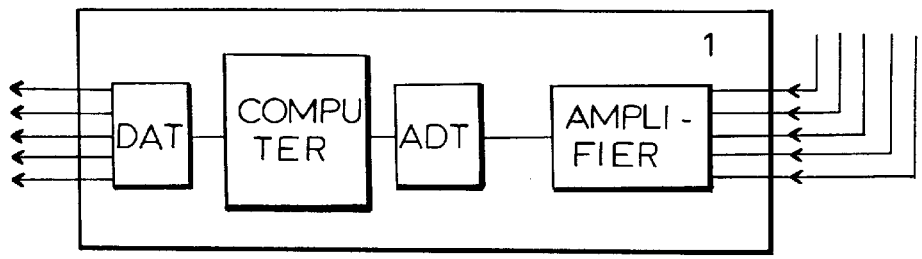
FIG. 5 represents the diagram of the control unit.

The example of claimed devices is the following:

The control unit 1 (FIG. 5) consists of amplifier of input signals with integrator, eight channel ten-rank analog-digital transformer (ADT) with serial interface max 192, processor PC-104 with quartz generator and eight channel thirteen-rank digital-analog transformer (DAT) with serial interface max 540. The output signals from DAT are the outputs of control unit 1 three of which (except the start-generation signals) conduct the signals determining the value of energy of capacities in the power supply 2.

The lasers are represented by YAG:Nd (wavelengths 1.06 $\mu$m or 1.32 $\mu$m), YAG:Ho (wavelength 2.09 $\mu$m) and YAG:Er (wavelength 2.94 $\mu$m). The dispersive element 28 is represented by glass prism. The photo detectors 29 are represented by Si photodiodes FD-256. The photo-electric detector of infra-red radiation 31 is represented by Ge photodiode FD-9. The comparator 30 is represented by microscheme K554CA3 or LM-111. The acoustic detector 34 is represented by microphone B&K4138.

Thus the offered devices providing the operative control with the opportunity to change in a wide range the parameters of laser radiation allow to carry out surgical procedures on tissues as scalpel, coagulator or destructor depending on required types, modes and combinations of lasers, oriented on minimum invasion effect.

I claim:

1. An assembly for laser tissue processing comprising:
a control unit (1) having a plurality of outputs connected to a laser power supply (2);
a first pulsed laser (3) having an optical axis and a wavelength;
a second pulsed laser (4) having an optical axis and a wavelength, said optical axis of said second laser (4) being parallel to said optical axis of said first pulsed laser (3);
a removable reflecting mirror (7) and a dichroic mirror (8), said dichroic mirror (8) being reflecting at said wavelength of said first laser (3) and transparent at said wavelength of said second laser (4), said mirrors (7, 8) being optically conjugated and placed on said optical axes of said first and second lasers (3, 4) respectively;
a first focusing system (9), an optical fiber (10) and a handpiece (11) placed on said optical axis of said second laser (4);
a second focusing system (12), an optical fiber (13) and a handpiece (14) placed on said optical axis of said first laser (3);
a detector (15) for determining a status of tissue, said detector (15) having an input which is conjugated with a place of laser influence on said tissue and an output which is connected to said control unit (1); and
a plurality of electronic switchers (5, 6) connected between said lasers (3, 4) and said laser power supply (2), each of said electronic switchers (5, 6) having an input which is connected to a respective output of said control unit (1).

2. The invention as defined in claim 1 wherein said detector (15) comprises a spectral analyzer (27) having a 200–1500 nm range and an input which is optically conjugated with said place of laser influence on said tissue and a dispersive element (28), a photodiode array (29) and a comparator (30).

3. The invention as defined in claim 1 wherein said detector (15) comprises an IR radiation photodetector (31) having an input which is optically conjugated with said place of laser influence on said tissue by a folding mirror (32) placed on said optical axis of one of said lasers (3, 4) between an output coupler of said one laser and one of said focusing systems (9, 12) through a spectral filter (33) to protect said photodetector (15) against laser radiation.

4. The invention as defined in claim 1 wherein said detector (15) comprises an acoustic detector (34) having a direction of maximum sensitivity, said acoustic detector (34) being placed so that an angle α between said direction of its maximum sensitivity and an optical axis at an output of one of said handpieces (11, 14) is within a range of: 11°<α<86°.

5. The invention as defined in claim 1 wherein said electronic switchers (5, 6) comprise semiconducting or vacuum devices.

6. The invention as defined in claim 1 additionally comprising a water spray system (17) having a pumping device (35) and an air compressor (36) with corresponding outputs being combined in said handpieces (11, 14), said air compressor (36) being supplied with a plurality of electromagnetic choppers (37, 38) connected to said control unit (1) through a plurality of delays (40, 41).

7. An assembly for laser tissue processing comprising:
a control unit (1) having a plurality of outputs connected to a laser power supply (2);
a first pulsed laser (3) having an optical axis and a wavelength;
a second pulsed laser (4) having an optical axis and a wavelength, said optical axis of said second laser (4) being parallel to said optical axis of said first pulsed laser (3);
a third pulsed laser (20) having an optical axis and a wavelength, said optical axis of said third laser (20) being parallel to said optical axis of said first pulsed laser (3);
a first removable reflecting mirror (7) and a first dichroic mirror (8), said first dichroic mirror (8) being reflecting at said wavelength of said first laser (3) and transparent at said wavelength of said second laser (4), said mirrors (7, 8) being optically conjugated and placed on said optical axes of said first and second lasers (3, 4) respectively;
a second removable reflecting mirror (21) and a second dichroic mirror (25), said second dichroic mirror (25) being reflecting at said wavelength of said third laser (20) and transparent at said wavelengths of said first and second lasers (3, 4), said second mirrors (21, 25) being optically conjugated and placed on said optical axis of said third laser (20);
a first focusing system (9), an optical fiber (10) and a handpiece (11) placed on said optical axis of said second laser (4);
a second focusing system (12), an optical fiber (13) and a handpiece (14) placed on said optical axis of said first laser (3);
a third focusing system (22), an optical fiber (23) and a handpiece (24) placed on said optical axis of said third laser (20);
a detector (15) for determining a status of tissue, said detector (15) having an input which is conjugated with a place of laser influence on said tissue and an output which is connected to said control unit (1); and
a plurality of electronic switchers (5, 6, 26) connected between said lasers (3, 4, 20) and said laser power supply (2), each of said electronic switchers (5, 6, 26) having an input which is connected to a respective output of said control unit (1).

8. The invention as defined in claim 7 wherein said detector (15) comprises a spectral analyzer (27) having a 200–1500 nm range and an input which is optically conjugated with said place of laser influence on said tissue and a dispersive element (28), a photodiode array (29) and a comparator (30).

9. The invention as defined in claim 7 wherein said detector (15) comprises an IR radiation photodetector (31) having an input which is optically conjugated with said place of laser influence on said tissue by a folding mirror (32) placed on said optical axis of one of said lasers (3, 4, 20) between an output coupler of said one laser and one of said focusing systems (9, 12, 22) through a spectral filter (33) to protect said photodetector (15) against laser radiation.

10. The invention as defined in claim 7 wherein said detector (15) comprises an acoustic detector (34) having a direction of maximum sensitivity, said acoustic detector (34) being placed so that an angle α between said direction of its maximum sensitivity and an optical axis at an output of one of said handpieces (11, 14, 24) is within a range of: 11°<α<86°.

11. The invention as defined in claim 7 wherein said electronic switchers (5, 6, 26) comprise semiconducting or vacuum devices.

12. The invention as defined in claim 7 additionally comprising a water spray system (17) having a pumping device (35) and an air compressor (36) with corresponding outputs being combined in said handpieces (11, 14, 24), said air compressor (36) being supplied with a plurality of electromagnetic choppers (37, 38, 39) connected to said control unit (1) through a plurality of delays (40, 41, 42).

* * * * *